US006468200B1

United States Patent
Fischi

(10) Patent No.: US 6,468,200 B1
(45) Date of Patent: Oct. 22, 2002

(54) SEGMENTED PERISTALTIC INTRA-AORTIC BALLOON PUMP

(76) Inventor: Michael C. Fischi, 3401 James St., Syracuse, NY (US) 13206

( * ) Notice: Subject to any disclaimer, the term of this patent is extended or adjusted under 35 U.S.C. 154(b) by 0 days.

(21) Appl. No.: 09/519,366

(22) Filed: Mar. 6, 2000

(51) Int. Cl.[7] .................................................. A61M 1/10
(52) U.S. Cl. ........................................ 600/18; 623/3.16
(58) Field of Search ...................... 600/16–18; 623/3.1, 623/3.16, 3.28; 604/101, 101.01, 101.05

(56) References Cited

U.S. PATENT DOCUMENTS

| | | | | |
|---|---|---|---|---|
| 3,504,662 A | * | 4/1970 | Jones ........................... | 600/18 |
| 3,692,018 A | * | 9/1972 | Goetz et al. ................ | 417/389 |
| 3,791,374 A | * | 2/1974 | Guarino ........................ | 600/17 |
| 3,939,820 A | * | 2/1976 | Grayzel ....................... | 417/394 |
| 4,902,272 A | | 2/1990 | Milder et al. ................. | 600/18 |

OTHER PUBLICATIONS

Torchiana et al., Intraaortic Balloon Pumping for Cardiac Support: Trends in Practice and Outcome, 1968 to 1995, 113 J. Thoracic and Cardiovascular Surg., 758 ff, 1997.
Kantrowitz, et al., Initial Clinical Experience with Intraaortic Balloon Pumping in Cardiogenic Shock, 203 JAMA, 135 ff, Jan. 1968.
Bengston et al., Prognosis in Cardiogenic Shock after Acute Myocardial Infarction in the Interventional Era, 20 JACC 1482, ff, Dec. 1992.
Waksman, et al., Intra–Aortic Balloon Counterpulsation Improves Survival in Cardiogenic Shock Complicating Acute Myocardial Infarction, 14 European Heart Journal, 14 ff, 1993.

Holmes et al., Contemporary Reperfusion Therapy for Cardiogenic Shock: The GUSTO–I Trial Experience, 26 JACC, 668, ff, Sep. 1995.
Anderson et al., Use of Intraaortic Balloon Counterpulsation in Patients Presenting With Cardiogenic Shock: Observations From the GUSTO–I Study, 30 JACC, 708, ff, Sep. 1997.
Ishihara et al., Effects of Intraaortic Balloon Pumping on Coronary Hemodynamics after Coronary Angioplasty in Patients with Acute Myocardial Infarction, 124 American Heart Journal, 133 ff, Nov. 1992.
Brodie et al., Intra–Aortic Balloon Counterpulsation Before Primary Percutaneous Transluminal Coronary Angioplasty Reduces Catheterization Laboratory Events in High–Risk Patients With Acute Myocardial Infarction, 84 Am. J. Of Cardiology, 18 ff, Jul. 1999.

(List continued on next page.)

Primary Examiner—Kennedy Schaetzle
(74) Attorney, Agent, or Firm—Bernhard P. Molldrem, Jr.

(57) ABSTRACT

An intra-aortic blood pump (IABP) includes a multiple-chamber balloon disposed at the distal portion of a catheter. The chambers are inflated sequentially beginning with the most distal, i.e., the chamber closest to the aortic root. This advances the blood in the downstream direction, i.e., towards the renal arteries and the lower body, enhancing cardiac output and reducing pumping load on the left ventricle. In a preferred arrangement, the chambers can be of successively larger volume from proximal to distal, i.e., in the downstream direction. The ports or apertures that communicate gas flow between the catheter lumen and the respective chambers are sized from larger to progressively smaller in the downstream direction. Only a single lumen is needed for the drive gas, i.e., helium, and the unit can be used with existing IABP equipment.

4 Claims, 3 Drawing Sheets

OTHER PUBLICATIONS

Santoro et al., Reperfusion Therapy in Cardiogenic Shock Complicating Acute Myocardial Infarction, 138 Am. Heart J., 126 ff, Aug. 1999.

Bates et al., The Use of Intraaortic Balloon Counterpulsation as an Adjunct to Reperfusion Therapy in Cardiogenic Shock, 65 Int. J. of Cardiology, S37 ff, 1998.

Mehlhorn et al., 30 Years Clinical Intra–aortic Balloon Pumping: Facts and Figures, 47 Thorac. Cardiovasc.Surg., 298 ff, 1999.

Barry et al., Cardiogenic Shock: Therapy and Prevention, 21 Clin. Cardiol., 72 ff, 1998.

Ross et al., A Randomized Trial Comparing Primary Angioplasty With a Strategy of Short–Acting Thrombolysis and Immediate Planned Rescue Angioplasty in Acute Myocardial Infarction. The PACT Trial, 34 JACC, 1954 ff, Dec. 1999.

Vitale, Mechanical Cardiac Assistance, 25 Intensive Care Med., 543 ff, 1999.

* cited by examiner

SEGMENTED PERISTALTIC INTRA-AORTIC BALLOON PUMP

BACKGROUND OF THE INVENTION

This invention relates to catheter-inserted medical and surgical devices, and is more particularly concerned with a balloon pump that is inserted into the aorta of a patient to enhance cardiac output and increase perfusion.

An intra-aortic balloon pump, or IABP, is a sausage-shaped balloon that is positioned in a patient's artery and is timed with the cardiac cycle to inflate during diastole (i.e., when the ventricle relaxes for filling) and to deflate during systole (i.e., when the ventricle contracts for pumping). The IABP is typically non-distensible and made of a polyurethane film.

The purpose of the IABP is to reduce left ventricular preload and afterload. This can reduce the pulmonary capillary wedge pressure by approximately 20%, and can decrease aortic systolic pressure by 10% to 20%. With the IABP in place, mean arterial pressure can increase by 30 to 40% secondary to enhanced diastolic blood pressure, and both cardiac output and stroke volume experience a moderate increase.

The IABP supports the heart by pressure unloading by means of volume displacement, but not from volume unloading. There can be up to 15% improvement in myocardial energy balance, depending on diastolic augmentation, left ventricular endiastolic pressure (filling during diastole), proper timing, balloon size, and coronary resistance.

The typical LABP has polyurethane double-lumen catheter, 8.5 F to 10.5 F, with a balloon with a capacity of 30 cc to 50 cc, and a pressure transducer mounted at the tip. The IABP is percutaneously inserted via a guidewire through the iliac artery, and is placed in the descending aorta above the renal arteries. Fluoroscopy is used to guide placement of the unit at this position.

An extracorporeal pumping unit inflates and deflates the catheter lumen with a suitable neutral drive gas, such as helium. Electrocardiograph leads provide timing information, such as the R wave, to estimate systole and the sensor at the catheter tip provides arterial waveforms, and these are used to time the inflation and deflation, and to assess the hemodynamic effects of the IABP.

The IABP may be indicated for several conditions, i.e., cardiogenic shock; as an adjunct to thrombolysis or PTCA (percutaneous transluminal coronary angioplasty) in AMI (acute myocardial infarction) to maintain vessel patency; prior to coronary artery bypass graft surgery in high risk patients; severe mitral regurgitation (mitral valve too loose); decompensated mitral stenosis (mitral valve too tight); as a bridge to transplant (if an organ is readily available); refractory congestive heart failure; mechanical complication of AMI, i.e., mitral regurgitation due to papillary involvement or ventricular septal defect; or unstable angina refractory to medical therapy.

The current IABP, in which a single balloon inflates, is bi-directional, that is, it pushes some of the blood forward, perfusing to the lower body, and also pushes some of the blood towards the aortic root. This has been considered as increasing blood flow into the arteries near the aortic root, i.e., to the coronary arteries. However, this device can cause other problems, as indicated below.

Complications can result when the IABP is employed, most commonly vascular problems, such as limb ischemia, compartment syndrome, mesentaeric infarction, aortic perforation or dissection. Other complications include balloon rupture, passage failure, thrombosis, and infection. Risk factors include peripheral vascular disease, diabetes myelitis, and tobacco use (smoking).

Contraindications include significant aortic insufficiency; aortic aneurysm/dissection; sepsis; peripheral vascular disease; atrial septal defect; patent foramen ovale; patent ductus arteriosi; or coagulopathy. Use is also contraindicated if there is no defined endpoint of revascularization or transplant.

With the current IABP the patient is confined to strict bed rest, with no hip flexion permitted beyond about 10–20 degrees.

A stiff aorta, which can be secondary to atherosclerosis, may prevent lateral distribution of inflation pressure with a conventional IABP, and resulting in a low intra-aortic pressure change. Aortic regurgitation, or AR, is a contraindication for a conventional IABP, because of the reverse pumping action.

A balloon pump of this general type is described in Milder et al. U.S. Pat. No. 4,902,272. In the Milder et al. patent the intra-aortic balloon pump has a central or main pumping balloon, and one or two valve balloons positioned on one or both sides of the main pumping balloon. The associated catheter has a separate lumen for each of the balloons, and the drive unit has to control the pressure separately for each of the balloons, i.e., each of the two or three associated lumens requires a separate gas conduit. The valve balloons assist in the directionality of blood flow, so that the flow is directed toward the heart during diastole. In some instances, the pumping balloon must be inflated more than once during systole. This arrangement can approximate a peristaltic action by inflating multiple times during each coronary cycle. However, the rather complex pumping cycle can be difficult to implement, and the need for the distal and proximal end balloons restricts the size of the main pumping balloon, thereby limiting the amount of stroke enhancement. Also, the need for a separate conduit to inflate and deflate the chambers in the described fashion increases the complexity of the device and increases the size of the catheter, making it less safe. It also requires a specially designed extracorporeal inflation/deflation device. All of this makes the design highly impractical.

OBJECTS AND SUMMARY OF THE INVENTION

Accordingly, it is an object of this invention to provide a minimally invasive, cost-effective, temporary left-ventricular assisting device to augment cardiac output in an acutely failing heart.

It is another object to provide an IABP that inflates and deflates through a single lumen of the associated catheter.

It is a further object to provide an IABP with a catheter that is compatible with existing IABP equipment.

In accordance with an aspect of the present invention, a segmented peristaltic intraaortic balloon pump employs a catheter that is adapted to be inserted into the aorta of a patient, and has a lumen adapted for passage of helium or another suitable a drive gas. A segmented balloon is positioned on the distal portion of the catheter and has three or more chambers in succession. In a preferred embodiment, first, second, and third chambers are arranged from distal to proximal on the catheter, and there are apertures formed in the catheter for communicating drive gas between the lumen and the chambers, respectively. This permits gas in the lumen to inflate and deflate the first, second and third chambers such that said chambers inflate in sequence from distal to proximal and then deflate in sequence from distal to proximal. A pumping device outside the patient's body is connected to the lumen at a proximal end of the catheter. The pumping device pumps the gas into and out from said lumen to inflate during systole and deflate during diastole. In a preferred mode the three (or more) chambers are successively larger in the direction from distal to proximal, i.e., with the smallest chamber being closest to the aortic root. Also, the apertures or openings from the lumen to the chambers are largest for the most distal, i.e., first, chamber and then progressively smaller for the second chamber, third chamber, and so on. This arrangement ensures that the first chamber will inflate first, then the second, and then the third, which causes peristaltic pumping toward the lower arteries. Similarly, the first chamber will deflate first, followed by the second chamber, and then the third chamber. This creates a negative pressure just prior to systole, to alleviate back pressure on the left ventricle, and relieves pumping load on the left ventricle. This also avoids flow towards the aortic root, which can cause problems if the patient's heart has aortic regurgitation.

The catheter can be inserted percutaneously through the iliac artery into the thoracic descending aorta. Helium is pumped into and out of the outer lumen or the catheter to the multiple inflatable chambers, while the inner lumen is used for pressure transduction. The chambers inflate in sequential order during early diastole, starting with the chamber most proximal to the aortic root to the chamber most distal from the aortic root. This order of balloon inflation pushes blood downstream in peristaltic fashion. The chambers will also deflate in a sequential order just prior to systole starting with the chamber most proximal to the aortic root. This sequence of deflation will generate a negative pressure in the aorta directed at the ventricle prior to systole, thus decreasing cardiac work load. The catheter inflation/deflation and timing can be accomplished using existing IABP equipment.

The above and many other objects, features, and advantages of this invention will become apparent to persons skilled in the art from the ensuing description of a preferred embodiment, which is to be read in conjunction with the accompanying Drawing.

DETAILED DESCRIPTION OF THE PREFERRED EMBODIMENT

Figure 1:
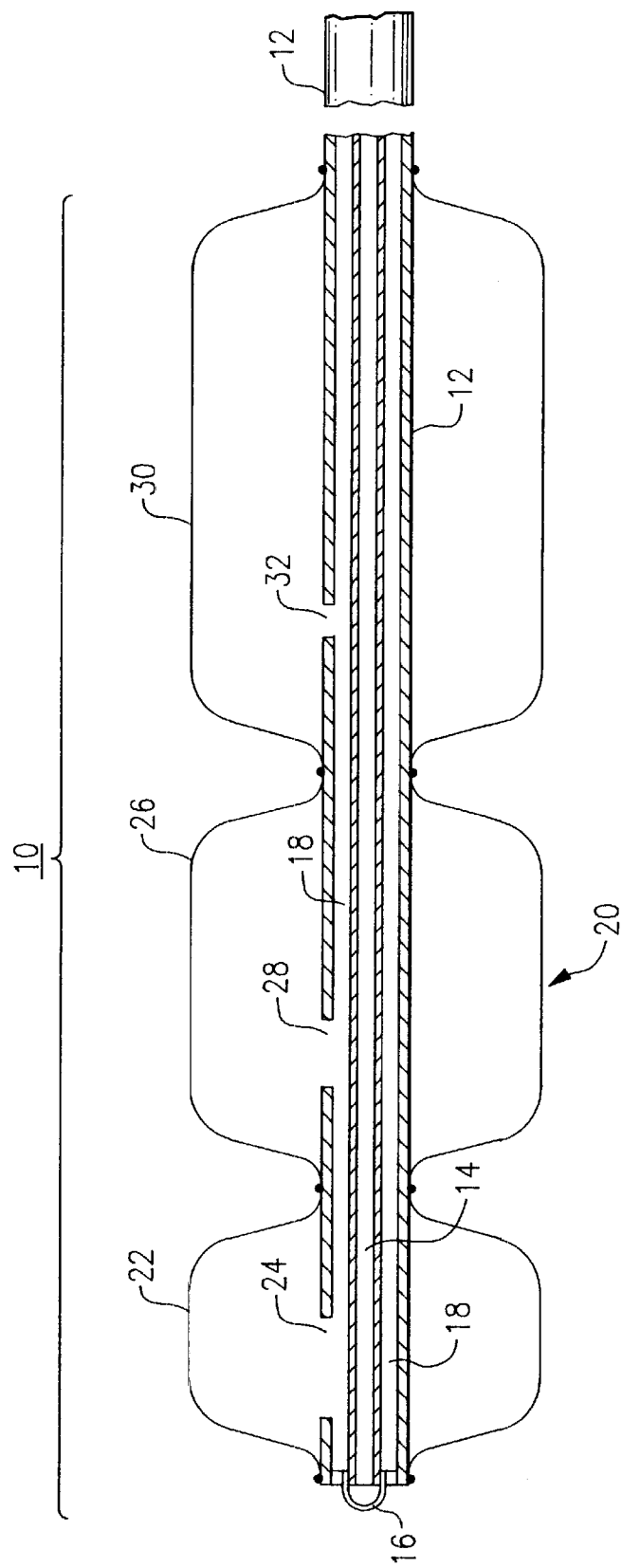
FIG. 1 is a schematic sectional view of an intra-aortic balloon pump according to one embodiment of this invention.

With reference to the Drawing, and initially to FIG. 1 thereof, an intra-aortic balloon pump or IABP 10 is here shown configured as a multiple-chamber peristaltic pump. A double-lumen polyurethane catheter 12 is provided with an inner lumen 14 for pressure sensing or similar instrumentation. A blood pressure sensor 16 is provided at the distal tip of the catheter 12 in communication with the inner lumen 14. An outer lumen 18 provides for passage of a drive gas, e.g., He, for inflation and deflation of a segmented balloon 20 that is situated on a distal portion of the catheter 12. The balloon 20 has a first, distal chamber 22 adapted to be positioned just distal to the left subclavian artery. An aperture 24 to the lumen 18 allows the drive gas to pass into and out of the chamber 22. A second chamber 26 adjacent the first chamber 22 has a larger volume than the chamber 22, and has an aperture 28 to the lumen 18. The aperture 28 is smaller than the aperture 24. A third chamber 30 is situated proximal of the second chamber 26, i.e., downstream in the aorta, and is of greater volume than the chamber 26. The third chamber has an aperture 32 to the outer lumen 18 that is smaller than the aperture 28. In this embodiment, the skin of the balloon 20 is a polyurethane film, which is selected for being flexible, but relatively inextensible. The balloon 20 is anchored to the catheter 12 by bands 34 between successive ones of the chambers 22, 26, 30.

Figure 2:
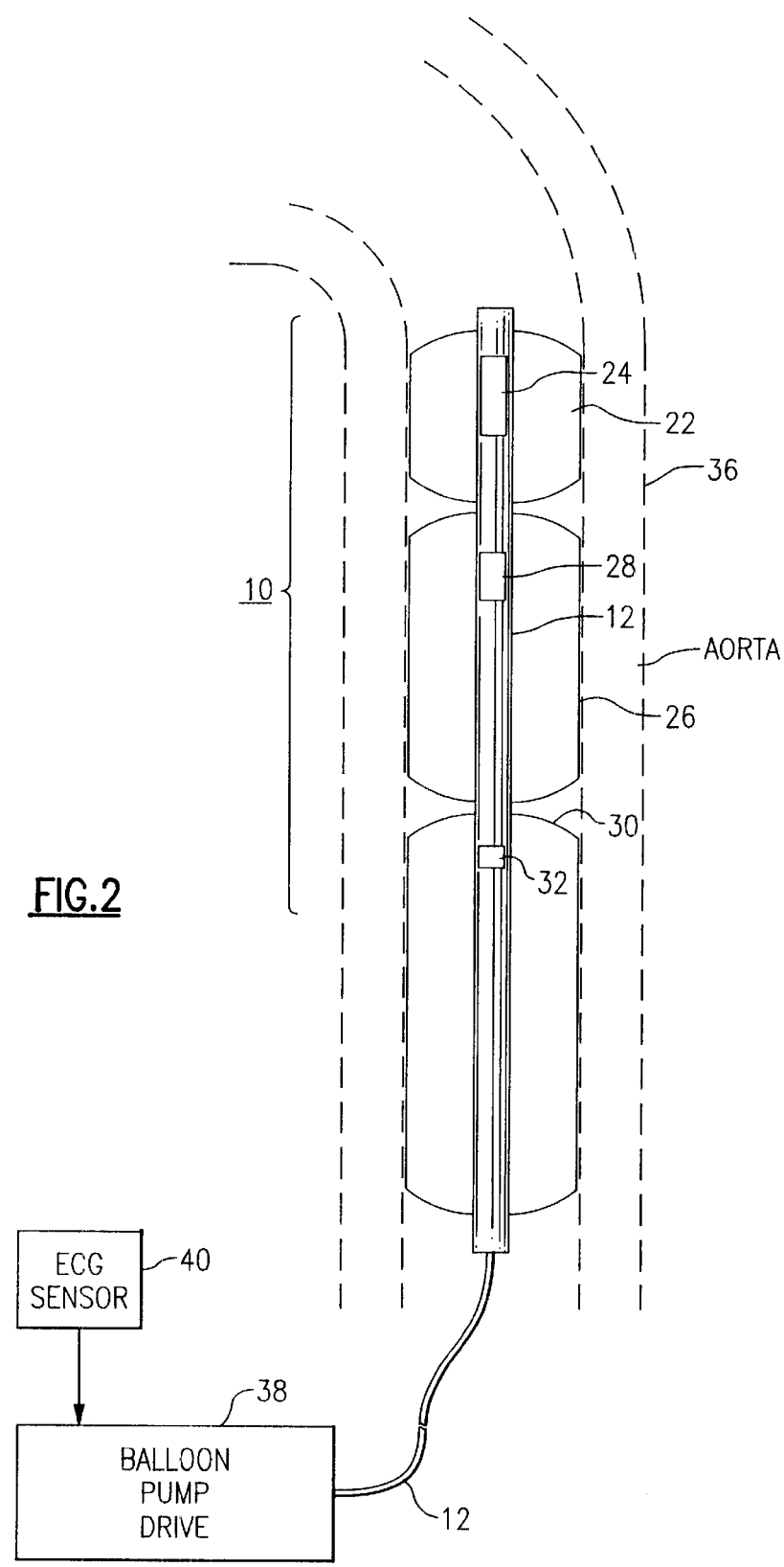
FIG. 2 is a schematic system view of this embodiment.

The IABP 10 is inserted percutaneously via a lower limb artery into the patient's descending aorta 36, to a position as shown in FIG. 2 above the renal arteries. A conventional balloon pump drive 38 external to the patient is attached to the proximal end of the catheter 12 to force helium into the lumen 18 and withdraw helium from it. An ECG sensor 40 obtains the patient's heart cycle, e.g., from the R-wave.

Figure 3:
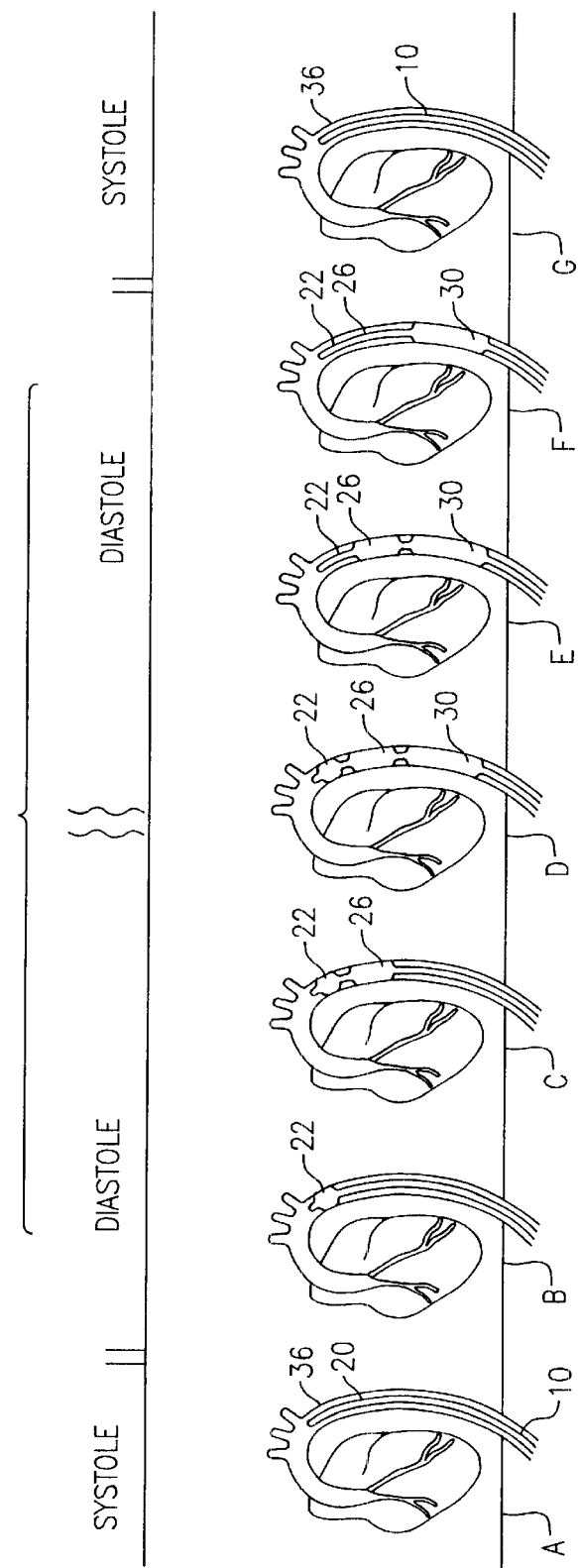
FIG. 3 illustrates the inflation and deflation sequence of this embodiment.

The pumping cycle of the segmented peristaltic IABP 10 is illustrated in FIG. 3. The balloon 20 is deflated during systole, and at the beginning of diastole begins to inflate. Because of the size differences in the chambers and in the respective apertures, the chamber 22 inflates first, as shown at B. The chambers inflate in sequence, with the chamber 26 inflating next (as shown at C), followed by inflation of the chamber 30 (shown at D). The effect of the sequential inflation of the chambers 22, 26, 30 is to push aortic blood downstream towards the renal arteries and the lower body. Then, just in advance of systole, the pump drive 38 withdraws helium from the catheter lumen 18, deflating the chambers in sequence beginning with the most distal or first chamber 22 (shown at E in FIG. 3). Then the second chamber 26 deflates (shown at F), and last the third chamber deflates (shown at G), leaving the balloon collapsed so that the aorta is open during systole. The effect of the sequential deflation is to draw blood away from the heart just prior to systole, thus reducing pumping load on the heart.

In the preferred embodiment, the catheter 12 can be size 9.5 F, for adults. For pediatric use, the size can be 7–9 F. The inflated chamber diameter is 16 mm, and the three chambers 22, 26, 30 can have volumes of about 6 cc, 12 cc, and 24 cc, respectively, for a total balloon volume of 42 cc. The priming volume is considered to be about 56 cc, which is larger than the total chamber volume due to catheter length, multiple connections, and compressibility of the gas. The helium inflation pressure is preferably about 9–10 psi.

The gas inlet ports or apertures are arranged so that the larger apertures are in the chambers more proximal to the aortic root. That is, the first chamber aperture 24 will be larger than the second aperture 28, the second larger than the third aperture 32, and so on for each successive chamber. There is less resistance to helium influx/efflux in the chambers nearer the aortic root, allowing them to inflate and deflate more rapidly.

The chambers 22, 26, 30 increase progressively in size in the direction downstream from the aortic root, i.e., from distal to proximal along the catheter 12. The smaller volume of the more distal chambers, and the smaller amount of blood that they will have to displace, allows them to inflate and deflate more rapidly than the larger, more proximal chambers.

The combination of the above two features produces sequential inflation and sequential deflation using a single lumen of a double lumen catheter, and utilizing standard, existing IABP hardware.

It may be possible using other techniques to effect sequential inflation and deflation of the balloon chambers, for example, using different stiffnesses of material in the respective chambers.

The balloon pump 10 of this invention follows a different philosophy from the conventional IABP, in that it does not so much favor directing the diastolic pressure backwards at the coronary arteries. Rather, the emphasis is placed on pushing the column of blood downstream so as to augment cardiac output and renal blood flow. Increased cardiac output and increased renal perfusion can reduce the need for chemical inotropes or vasoconstrictors, as the latter are associated with increased mortality. Nevertheless, in this design there will still be some back pressure generated from the inflation of the first balloon chamber 22. This design also creates more negative pressure than a conventional IABP for the left ventricle prior to systole because of the sequential deflation, thereby reducing cardiac workload, by decreasing the left ventricular end diastolic pressure. Preliminary testing shows that this design generates superior forward flow in the horizonal plane, as compared to a conventional IABP.

The peristaltic sequentially inflating, multi-chamber IABP of this invention can serve as an effective tool for use in the management of cardiogenic shock; can be used after AMI as a bridge to revascularization, in combination with lytics if appropriate; or can provide pre-operative optimization in high-risk heart patients.

While the invention has been described in detail with respect to a preferred embodiment, it should be recognized that there are many alternative embodiments that would become apparent to persons of skill in the art. Many modifications and variations are possible which would not depart from the scope and spirit of this invention, as defined in the appended claims.

I claim:

1. A segmented peristaltic intraaortic balloon pump comprising
   a catheter adapted to be inserted into an aorta and having a lumen therein adapted for passage of a drive gas;
   a segmented balloon positioned on a distal portion of said catheter and having at least first, second, and third chambers arranged from distal to proximal thereon, with apertures formed in said catheter for communication of drive gas between said lumen and said chambers, respectively, to permit gas in said lumen to inflate and deflate said first, second and third chambers such that said chambers inflate in sequence from distal to proximal and then deflate in sequence from distal to proximal; and
   a pumping device coupled to said lumen at a proximal portion of said catheter for selectively pumping said drive gas into and out from said lumen;
   wherein said first, second and third chambers are of progressively larger volume from distal to proximal.

2. A segmented peristaltic intraaortic balloon pump comprising
   a catheter adapted to be inserted into an aorta and having a lumen therein adapted for passage of a drive gas;
   a segmented balloon positioned on a distal portion of said catheter and having at least first, second, and third chambers arranged from distal to proximal thereon, with apertures formed in said catheter for communication of drive gas between said lumen and said chambers, respectively, to permit gas in said lumen to inflate and deflate said first, second and third chambers such that said chambers inflate in sequence from distal to proximal and then deflate in sequence from distal to proximal; and
   a pumping device coupled to said lumen at a proximal portion of said catheter for selectively pumping said drive gas into and out from said lumen;
   wherein the apertures associated with said first, second, and third chambers are of progressively reduced effective area, from the first chamber to the third chamber, respectively.

3. A segmented peristaltic intraaortic balloon pump comprising
   a catheter adapted to be inserted into an aorta and having a lumen therein adapted for passage of a drive gas;
   a segmented balloon positioned on a distal portion of said catheter and having at least first, second, and third chambers arranged from distal to proximal thereon, with apertures formed in said catheter for communication of drive gas between said lumen and said chambers, respectively, to permit gas in said lumen to inflate and deflate said first, second and third chambers such that said chambers inflate in sequence from distal to proximal and then deflate in sequence from distal to proximal; and
   a pumping device coupled to said lumen at a proximal portion of said catheter for selectively pumping said drive gas into and out from said lumen;
   wherein said first, second, and third chambers have volumes on the order of 6 cc, 12 cc, and 24 cc, respectively.

4. A segmented peristaltic intraaortic balloon pump comprising
   a catheter adapted to be inserted into an aorta and having a lumen therein adapted for passage of a drive gas;
   a segmented balloon positioned on a distal portion of said catheter and having at least first, second, and third chambers arranged from distal to proximal thereon, with apertures formed in said catheter for communication of drive gas between said lumen and said chambers, respectively, to permit gas in said lumen to inflate and deflate said first, second and third chambers such that said chambers inflate in sequence from distal to proximal and then deflate in sequence from distal to proximal; and
   a pumping device coupled to said lumen at a proximal portion of said catheter for selectively pumping said drive gas into and out from said lumen;
   wherein said second chamber is about twice the volume of the first chamber, and the third chamber is about four times the volume of the first chamber.

* * * * *